United States Patent [19]

Arnold

[11] Patent Number: 5,523,419
[45] Date of Patent: Jun. 4, 1996

[54] PROCESS FOR SEPARATING TRIOXANE FROM AN AQUEOUS MIXTURE

[75] Inventor: Dieter Arnold, Königstein/Taunus, Germany

[73] Assignee: Hoechst Aktiengesellschaft, Frankfurt, Germany

[21] Appl. No.: 144,883

[22] Filed: Oct. 28, 1993

[30] Foreign Application Priority Data

Oct. 31, 1992 [DE] Germany ............................ 42 36 853.7

[51] Int. Cl.$^6$ ................................................. C07D 323/06
[52] U.S. Cl. ................................................. 549/368
[58] Field of Search ............................................. 549/368

[56] References Cited

U.S. PATENT DOCUMENTS

| 4,043,873 | 8/1977 | Ackermann et al. | 549/368 |
| 4,493,752 | 1/1985 | Naito et al. | 549/368 |
| 5,061,349 | 10/1991 | Küppenbender et al. | 549/368 |

FOREIGN PATENT DOCUMENTS 0133669  3/1985  European Pat. Off. .

OTHER PUBLICATIONS

Chemical Abstract, vol. 118 No. 214535, Bastioli et al., 1992, "Selectively permeable membranes and their use".

Chemical Abstract, vol. 116 No. 132080, Hanemaaijer et al., 1991 "Membrane separation for dehydrating a gas, vapor, or liquid mixture".

Chemical Abstract, vol. 113 No. 174,481, Pasternak et al., 1990, "Process are membranes for the concentration of aqueous ketone".

Dialog Database Abstract for German Patent DE 3328126, Aug. 4, 1983.

*Primary Examiner*—C. Warren Ivy
*Assistant Examiner*—Raymond Covington
*Attorney, Agent, or Firm*—Curtis, Morris & Safford

[57] ABSTRACT

In a process for separating trioxane from an aqueous mixture consisting essentially of trioxane, water and formaldehyde, water is extracted from the mixture by pervaporation and the water-depleted mixture (retentate) is separated by rectification into trioxane and an azeotropic mixture of trioxane, water and formaldehyde.

4 Claims, 1 Drawing Sheet

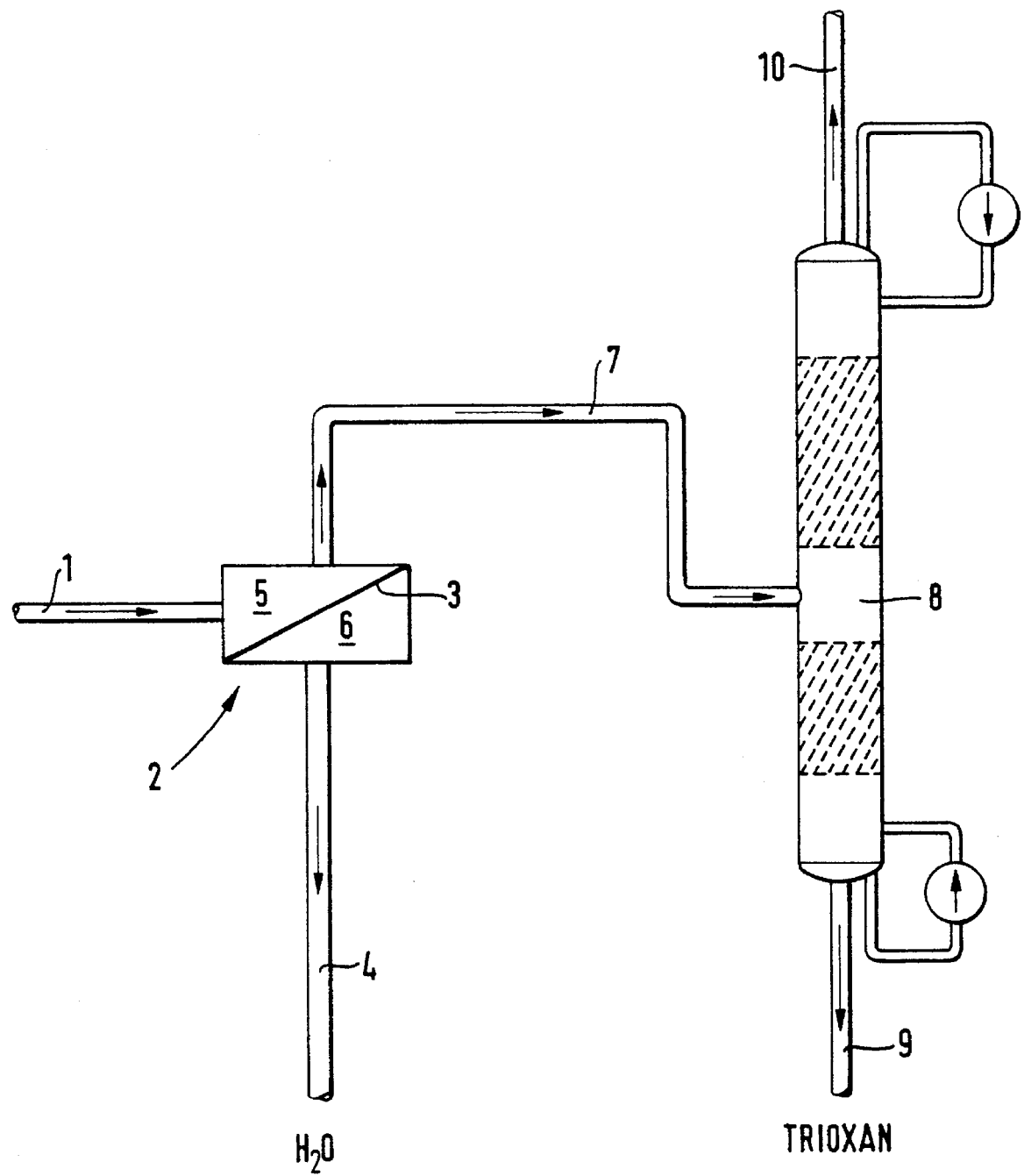

PROCESS FOR SEPARATING TRIOXANE FROM AN AQUEOUS MIXTURE

DESCRIPTION

The preparation of trioxane gives rise to an azeotropic mixture consisting essentially of trioxane, water and formaldehyde. From this mixture trioxane is extractively separated with the aid of an azeotrope-former such as methylene chloride or benzene. In a subsequent distillation the azeotrope-former is recovered and returned to the extractive distillation. In this process large amounts of azeotrope-former need to be used and recovered with high energy consumption. Disposal of unavoidable boilable emissions is costly, since methylene chloride and benzene are classified as dangerous pollutants.

It is an object of the present invention to provide a remedy. The invention achieves this object by extracting water from the mixture by pervaporation and separating the water-depleted mixture (retentate) by rectification into trioxane and an azeotropic mixture of trioxane, water and formaldehyde.

The pervaporation can be carried out at temperatures of from 70° to 120° C. using a membrane of polyvinyl alcohol at pressures of from i to 3 bar on the retentate side and from 30 to 150 mbar on the permeate side.

The advantages of the process of the invention are essentially that no additional component (such as azeotrope-former) is required, thus causing the emission problem to disappear and lowering the energy consumption (lower temperature level). Furthermore, the pervaporation unit occupies less space than the extractive distillation equipment at a comparable throughput.

BRIEF DESCRIPTION OF THE DRAWING

An embodiment of the invention will now be more particularly described by way of example with reference to the figure.

An aqueous mixture (line 1) containing 65% by weight of trioxane, 27.5% by weight of water and 7.5% by weight of formaldehyde is treated in a pervaporation unit 2, comprising a membrous 3 of polyvinyl alcohol from GFT (Gesellschaft für Trenntechnik mbH, D-6680 Neunkirchen/Saar), to remove water (line 4).

The separation is carried out at 90° C. The pressure is 1 bar on the retentate side 5, (50 mbar) on the permeate side 6. The permeate obtained is water and the retentate obtained is a mixture of 84% by weight of trioxane, 10% by weight of formaldehyde and 6% by weight of water (line 7). The retentate is separated in a rectification column 8 at atmospheric pressure into pure trioxane (bottom product, line 9) and an azeotropic mixture of trioxane, formaldehyde and water (top product, line 10).

What is claimed is:

1. A process for separating trioxane from an aqueous mixture consisting essentially of trioxane, water and formaldehyde, which comprises extracting water from the mixture by pervaporation and separating the water-depleted mixture (retentate) by rectification into trioxane and an azeotropic mixture of trioxane, water and formaldehyde.

2. The process as claimed in claim 1, wherein pervaporation is carried out using a membrane of polyvinyl alcohol at a temperature of from 70° to 120° C. and a pressure of from 1 to 3 bar on the retentate side and from 30 to 150 mbar on the permeate side.

3. The process as claimed in claim 1, wherein the pervaporation is carried out using a membrane of polyvinyl alcohol.

4. The process as claimed in claim 1, wherein the pervaporation is carried out at a temperature of from 70° to 120° C.

* * * * *